United States Patent
Navarro et al.

(10) Patent No.: US 6,605,613 B2
(45) Date of Patent: Aug. 12, 2003

(54) MACROLIDES

(75) Inventors: François Navarro, Bruebach (FR); Samuel Petit, Mont Saint-Aignan (FR); Guy Stone, Ettingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/866,977

(22) Filed: May 29, 2001

(65) Prior Publication Data

US 2002/0032213 A1 Mar. 14, 2002

Related U.S. Application Data

(63) Continuation of application No. PCT/EP99/09521, filed on Dec. 6, 1999.

(30) Foreign Application Priority Data

Dec. 7, 1998 (GB) ................................................ 9826882
Mar. 4, 1999 (GB) ................................................ 9904934

(51) Int. Cl.$^7$ .................... C07D 498/18; A61K 31/715; A61K 47/10

(52) U.S. Cl. ........................................ 514/291; 540/456
(58) Field of Search ........................... 540/456; 514/291

(56) References Cited

U.S. PATENT DOCUMENTS

| 4,049,128 A | 9/1977 | Jeffrey .......................... 213/1.6 |
| 4,080,445 A | 3/1978 | Lin et al. ...................... 424/227 |

FOREIGN PATENT DOCUMENTS

| EP | 0041795 | 12/1981 |
| EP | 0 329460 | 8/1989 |
| EP | 0423714 | 4/1991 |
| WO | WO 94/09010 | 4/1994 |
| WO | WO 97/03654 | 2/1997 |
| WO | WO 98/04279 | 2/1998 |
| WO | WO 98/33482 | 8/1998 |

*Primary Examiner*—Bruck Kifle
(74) *Attorney, Agent, or Firm*—John D. Thallemer

(57) ABSTRACT

A mixture comprising a poly-ene macrolide and an antioxidant. Preferably, the poly-ene macrolide is rapamycin and the antioxidant is 2,6-di-tert.-butyl-4-methylphenol. The presence of the antioxidant improves the stability of the poly-ene macrolide to oxidation.

5 Claims, No Drawings

MACROLIDES

This application is a continuation of International Application No. PCT/EP99/09521, filed Dec. 6, 1999, the contents of which are incorporated herein by reference.

The present invention relates to the stabilization of a pharmaceutically active ingredient sensitive to oxidation, e.g. a poly-ene macrolide, preferably a poly-ene macrolide having immunosuppressant properties, particularly rapamycins.

The handling and storage particularly in the bulk form of pharmaceutically active ingredients which are sensitive to oxidation is difficult. Special handling is necessary and often the oxidation-sensitive ingredient is stored in air-tight packaging under protective gas. Substantial amounts of stabilizers are added during the formulating process of such pharmaceutically active ingredients.

Poly-ene macrolides have satisfactory stability properties. However, it has now been found that their stability to oxygen may substantially be improved by the addition of a stabilizer, e.g. an antioxidant, during their isolation step.

According to the invention, there is provided

1. A process for stabilizing a poly-ene macrolide comprising adding an antioxidant to the purified macrolide, preferably at the commencement of its isolation step.

This process is particularly useful for the production of a stabilized poly-ene macrolide in bulk. The amount of antioxidant may conveniently be up to 1%, more preferably from 0.01 to 0.5% (based on the weight of the macrolide). Such a small amount is referred to hereinafter as a catalytic amount.

As alternatives to the above the present invention also provides:

2. A mixture, e.g. a bulk mixture, comprising a poly-ene macrolide and an anti-oxidant, preferably a catalytic amount thereof, preferably in solid form.

The mixture may be in particulate form e.g. cristallized or amorphous form. It may be in a sterile or substantially sterile condition, e.g. in a condition suitable for pharmaceutical use.

3. Use of a mixture as defined above in 2. in the manufacture of a pharmaceutical composition.

Examples of poly-enes macrolides are e.g. molecules comprising double bonds, preferably conjugated double bonds, for example such having antibiotic and/or immunosuppressant properties, e.g. macrolides comprising a lactam or lactone bond and their derivatives, e.g. compounds which have a biological activity qualitatively similar to that of the natural macrolide, e.g. chemically substituted macrolides. Suitable examples include e.g. rapamycins and ascomycins. A preferred poly-ene macrolide is a macrolide comprising at least 2 conjugated double bonds, e.g. 3 conjugated double bonds.

Rapamycin is a known lactam macrolide produceable, for example by *Streptomyces hygroscopicus*. The structure of rapamycin is given in Kessler, H. et al.; 1993; Helv. Chim. Acta, 76: 117. Rapamycin has antibiotic and immunosuppressant properties. Derivatives of rapamycin are known, e.g. 16-O-substituted rapamycins, for example as disclosed in WO 94/02136 and WO 96/41807, 40-O-substituted rapamycins, for example as disclosed in WO 94/09010, WO 92/05179, WO 95/14023, 94/02136, WO 94/02385 and WO 96/13273, all of which being incorporated herein by reference. Preferred rapamycin derivatives are e.g. rapamycins wherein the hydroxy in position 40 of formula A illustrated at page 1 of WO 94/09010 is replaced by —OR wherein R is hydroxyalkyl, hydroxyalkoxyalkyl, acylaminoalkyl or aminoalkyl, e.g. 40-O-(2-hydroxy)ethyl-rapamycin, 40-O-(3-hydroxy)propyl-rapamycin, and 40-4-[2-(2-hydroxy)ethoxy]ethyl-rapamycin.

Ascomycins, of which FK-506 and ascomycin are the best known, form another class of lactam macrolides, many of which have potent immunosuppressive and anti-inflammatory activity. FK506 is a lactam macrolide produced by *Streptomyces tsukubaensis*. The structure of FK506 is given in the Appendix to the Merck Index, 11th ed. (1989) as item A5. Ascomycin is described e.g. in U.S. Pat. No. 3,244,592. Ascomycin; FK506, other naturally occurring macrolides having a similar biological activity and their derivatives, e.g. synthetic analogues and derivatives are termed collectively "Ascomycins". Examples of synthetic analogues or derivatives are e.g. halogenated ascomycins, e.g. 33-epi-chloro-33-desoxy-ascomycin such as disclosed in EP-A-427,680, tetrahydropyran derivatives, e.g. as disclosed in EP-A-626,385.

Particularly preferred macrolides are rapamycin and 40-O-(2-hydroxy)ethyl-rapamycin.

Preferred antioxidants are for example 2,6-di-tert.-butyl-4-methylphenol (hereinafter BHT), vitamin E or C, BHT being particularly preferred.

A particularly preferred mixture of the invention is a mixture of rapamycin or 40-O-(2-hydroxy)ethyl-rapamycin and 0.2% (based on the weight of the macrolide) of antioxidant, preferably BHT.

The antioxidant may be added to the poly-ene macrolide at the commencement of the isolation steps, preferably the final isolation step, more preferably just prior to the final precipitation step. The macrolide is preferably in a purified state. It may be dissolved in an inert solvent and the antioxidant is added to the resulting solution, followed by a precipitation step of the stabilized macrolide, e.g. in an amorphous form or in the form of crystals. Preferably the mixture of the invention is in amorphous form.

The resulting stabilized macrolide exhibits surprisingly an improved stability to oxidation and its handling and storage, e.g. in bulk form prior to its further processing for example into a galenic composition, become much easier. It is particularly interesting for macrolides in amorphous form.

The macrolide stabilized according to the invention may be used as such for the production of the desired galenic formulation. Such formulations may be prepared according to methods known in the art, comprising the addition of one or more pharmaceutically acceptable diluent or carrier, including the addition of further stabilizer if required.

Accordingly there is further provided:

4. A pharmaceutical composition comprising, as active ingredient, a stabilized mixture as disclosed above, together with one or more pharmaceutically acceptable diluent or carrier.

The composition of the invention may be adapted for oral, parenteral, topical (e.g. on the skin), occular, nasal or inhalation (e.g. pulmonary) administration. A preferred composition is one for oral administration, preferably a water-free composition when the active ingredient is a lactone macrolide.

The pharmaceutical compositions of the invention may comprise further excipients, e.g. a lubricant, a disintegrating agent, a surfactant, a carrier, a diluent, a flavor enhancer, etc. It may be in liquid form, e.g. solutions, suspensions or emulsions such as a microemulsions, e.g. as disclosed in U.S. Pat. No. 5,536,729, or in solid form, e.g. capsules, tablets, dragées, powders (including micronized or otherwise reduced particulates), solid dispersions, granulates, etc., e.g. as disclosed in WO 97/03654, the contents of which being incorporated herein by reference, or semi-solid forms such as ointments, gels, creams and pastes. They are preferably adapted to be in a form suitable for oral administration. Preferably they are in solid form. The pharmaceutical compositions of the invention may be prepared according to known methods, by mixing the macrolide stabilized according to the invention with the additional ingredients under stirring; the ingredients may be milled or ground and if desired compressed, e.g into tablets.

This invention is particularly interesting for rapamycin compositions in liquid or solid form. A particularly preferred composition is a solid dispersion, e.g. comprising a stabilized rapamycin according to the invention and a carrier medium, e.g. a water-soluble polymer such as hydroxypropylmethylcellulose, e.g. as disclosed in WO 97/03654.

The compositions of the invention are useful for the indications as known for the macrolide they contain at e.g. known dosages. For example, when the macrolide has immunosuppressant properties, e.g. rapamycin or a rapamycin derivative, the composition may be useful e.g. in the treatment or prevention of organ or tissue acute or chronic allo- or xeno-transplant rejection, autoimmune diseases or inflammatory conditions, asthma, proliferative disorders, e.g tumors, or hyperproliferative vascular disorders, preferably in the prevention or treatment of transplant rejection.

The amount of macrolide and of the composition to be administered depend on a number of factors, e.g. the active ingredient used, the conditions to be treated, the duration of the treatment etc. For e.g. rapamycin or 40-O-(2-hydroxy) ethyl-rapamycin, a suitable daily dosage form for oral administration comprise from 0.1 to 10 mg, to be administered once or in divided form.

In another aspect, this invention also provides 40-O-(2-hydroxy)ethyl-rapamycin in a crystalline form, particularly in a substantially pure form. Preferably the crystal form is characterized by the absence or substantial absence of any solvent component; it is in non-solvate form.

40-O-(2-hydroxy)ethyl-rapamycin in crystalline form belongs to the monoclinic sytem. The resulting crystals have a m.p. of 146°–147° C., especially 146.5° C. To assist identification of the new crystalline form, X-ray diffraction analysis data are provided. The conditions under which these data are obtained are as follows:

| | |
|---|---|
| Temperature | 293(2)K |
| Wavelength | 1.54178Å |
| Space group | P2$_1$ |
| Unit cell dimensions | |
| a | 14.378.(2)Å |
| b | 11.244(1)Å |
| c | 18.310(2)Å |
| β | 108.58(1)° |
| Volume | 2805.8(6)Å$^3$ |
| Z | 2 |
| Density (calculated) | 1.134 g/cm$^3$ |
| Absorption coefficient | 0.659 mm$^{-1}$ |
| F(000) | 1040 |
| Crystal size | 0.59 × 0.11 × 0.03 mm |
| θ range for data collection | 2.55 to 57.20° |
| Reflections collected | 4182 |
| Independent reflections | 4037 [R(int) = 0.0341] |
| Intensity decay | 32% |
| Refinement method | Full-matrix least-squares on F$^2$ |
| Data/restraints/parameters | 3134/1/613 |
| Goodness-of-fit on F$^2$ | 1.055 |
| Final R Indices [I > 2 sigma(I)] | R$_1$ = 0.0574, wR$_2$ = 0.1456 |
| Largest diff. peak and hole | 0.340 and −0.184 e/Å$^3$ |

40-O-(2-hydroxy)ethyl-rapamycin in crystalline form may be prepared by dissolving the amorphous compound in a solvent e.g. ethyl acetate and adding an aliphatic hydrocarbon $C_nH_{2n+2}$(n=5, 6 or 7). After addition of the hydrocarbon, the resulting mixture may be warmed e.g. at a temperature of 25 to 50° C., e.g. up to 30–35° C. Storing of the resulting mixture may conveniently take place at a low temperature, e.g. below 25° C., preferably from 0 to 25° C. The crystals are filtered and dried. Heptane is preferred as an aliphatic hydrocarbon. If desired, nucleation procedures may be commenced e.g. by sonication or seeding.

The present invention also provides a process for purifying 40-O-(2-hydroxy)ethyl-rapamycin comprising crystallizing 40-O-(2-hydroxy)ethyl-rapamycin from a crystal bearing medium, e.g. as disclosed above, and recovering the crystals thus obtained. The crystal bearing medium may include one or more components in addition to those recited above. A particularly suitable crystal bearing medium has been found to be one comprising ca. 2 parts ethyl acetate and ca. 5 parts aliphatic hydrocarbon, e.g. heptane.

40-O-(2-hydroxy)ethyl-rapamycin in crystalline form has been found to possess in vitro and in vivo immunosuppressive activity comparable to that of the amorphous form. In the localized GvHD, maximal inhibition (70–80%) of lymph node swelling is achieved with a dosage of 3 mg with 40-O-(2-hydroxy)ethyl-rapamycin in crystalline form.

40-O-(2-hydroxy)ethyl-rapamycin may be useful for the same indications as known for the amorphous compound, e.g. to prevent or treat acute and chronic allo- or xeno-transplant rejection, autoimmune diseases or inflammatory conditions, asthma, proliferative disorders, e.g tumors, or hyperproliferative vascular disorders, e.g as disclosed in WO 94/09010 or in WO 97/35575, the contents thereof being incorporated herein by reference. In general, satisfactory results are obtained on oral administration at dosages on the order of from 0.05 to 5 or up to 20 mg/kg/day, e.g. on the order of from 0.1 to 2 or up to 7.5 mg/kg/day administered once or, in divided doses 2 to 4×per day. Suitable daily dosages for patients are thus on the order of up to 10 mg., e.g. 0.1 to 10 mg.

40-O-(2-hydroxy)ethyl-rapamycin in crystalline form may be administered by any conventional route, e.g. orally, for example tablets or capsules, or nasallly or pulmonary (by inhalation). It may be administered as the sole active ingredient or together with other drugs, e.g. immunosuppressive and/or immunomodulatory and/or anti-inflammatory agents, e.g. as disclosed in WO 94/09010.

In accordance with the foregoing, the present invention also provides:

5. A method for preventing or treating acute or chronic allo- or xeno-transplant rejection, autoimmune diseases or inflammatory conditions, asthma, proliferative disorders, or hyperproliferative vascular disorders, in a subject in need of such treatment, which method comprises administering to said subject a therapeutically effective amount of 40-O-(2-hydroxy)ethyl-rapamycin in crystalline form;

6. 40-O-(2-hydroxy)ethyl-rapamycin in crystalline form for use as a pharmaceutical; e.g. in a method as disclosed above:

7. A pharmaceutical composition comprising 40-O-(2-hydroxy)ethyl-rapamycin in crystalline form together with a pharmaceutically acceptable diluent or carrier therefor;

8. A kit or package for use in immunosuppression or inflammation, including a pharmaceutical composition as disclosed above and a pharmaceutical composition comprising an immunosuppressant or immunomodulatory drug or an anti-inflammatory agent.

The following examples illustrate the invention without limiting it.

EXAMPLE 1

Crystallisation 0.5 g amorphous 40-O-(2-hydroxy)ethyl-rapamycin is dissolved in 2.0 ml ethyl acetate at 40° C. 5.0 ml heptane is added and the solution becomes "milky". After warming to 30° C., the solution becomes clear again. Upon cooling to 0° C. and with scratching an oil falls out of the solution. The test tube is closed and stored at 10° C. overnight. The resulting white voluminous solid is then filtered and washed with 0.5 ml of a mixture of ethyl acetate/hexane (1:2.5) and the resulting crystals are dried at 40° C. under 5 mbar for 16 hours. 40-O-(2-hydroxy)ethyl-rapamycin in crystalline form having a m.p. of 146.5° C. is thus obtained.

Crystallisation at a larger scale may be performed as follows: 250 g amorphous 40-O-(2-hydroxy)ethyl-rapamycin is dissolved in 1.0 l ethyl acetate under argon with slow stirring. This solution is heated at 30° C. and then during 45 minutes, 1.5 l heptane is added dropwise. 0.25 g of seed crystals prepared as disclosed above are added under the same conditions in portions. The mixture is further stirred at 30° C. over a period of 2 hours and the crystallisation mixture is cooled to 25° C. over 1 hour and then to 10° C. for 30 minutes and filtered. The crystals are washed with 100 ml of a mixture ethyl acetate/hexane (2:3). Subsequent drying is performed at 50° C. and ca 5 mbar. m.p. 146.5° C. IR in KBr 3452, 2931, 1746, 1717, 1617, 1453, 1376, 1241, 1191, 1163, 1094, 1072, 1010, 985, 896 cm$^{-1}$ Single X-ray structure with Coordinates are indicated in Tables 1 to 3 below.

EXAMPLE 2

Production of Stabilized 40-O-(2-hydroxy)ethyl-rapamycin 100 g 40-O-hydroxy)ethyl-rapamycin are dissolved in 600 l abs. ethanol. After addition of 0.2 g BHT, the resulting solution is added dropwise with stirring to 3.0 l water within 1 hour. The resulting suspension is stirred for an additional 30 minutes. Filtration with subsequent washing (3×200 ml water/ethanol at a v/v ratio of 5:1) results in a moist white product which is further dried under vacuum (1 mbar) at 30° C. for 48 hours. The resulting dried product contains 0.2% (w/w) BHT.

The resulting product shows improved stability on storage. The sum of by-products and degradation products in % after 1 week storage are as follows:

| Compound | 50° C. in open flask |
|---|---|
| Ex. 2 (0.2% BHT) | 1.49 |
| Without BHT | >10 |

The procedure of above Example may be repeated but using, as active ingredient, rapamycin.

TABLE 1

Atomic coordinates and equivalent isotropic displacement parameters (Å$^2$)

|  | x/a | y/b | z/c | U(eq) |
|---|---|---|---|---|
| C(1) | .9065(6) | .0121(9) | .5077(5) | .060(2) |
| O(1) | .9239(4) | −.0736(6) | .5482(4) | .076(2) |
| C(2) | .8041(5) | .0615(8) | .4625(4) | .060(2) |
| C(3) | .7847(7) | .1748(10) | .4984(6) | .087(3) |
| C(4) | .7627(7) | .1515(10) | .5725(7) | .098(3) |
| C(5) | .6795(7) | .0653(11) | .5610(6) | .094(3) |
| C(6) | .7005(6) | −.0496(9) | .5256(5) | .074(3) |
| N(7) | .7272(4) | −.0269(6) | .4567(4) | .059(2) |
| C(8) | .6781(5) | −.0693(7) | .3883(5) | .055(2) |
| O(8) | .6965(4) | −.0432(6) | .3287(3) | .074(2) |
| C(9) | .5940(6) | −.1566(8) | .3784(5) | .056(2) |
| O(9) | .6074(4) | −.2513(6) | .4074(4) | .084(2) |
| C(10) | .4962(5) | −.1136(8) | .3223(5) | .059(2) |
| O(10) | .5045(4) | −.1009(6) | .2486(3) | .075(2) |
| C(11) | .4079(6) | −.1951(8) | .3160(5) | .068(2) |
| C(11M) | .4107(7) | −.3114(9) | .2776(6) | .088(3) |
| C(12) | .3135(6) | −.1252(10) | .2738(6) | .088(3) |
| C(13) | .3099(6) | −.0061(10) | .3115(7) | .099(4) |
| C(14) | .4002(6) | .0651(9) | .3156(6) | .078(3) |
| O(14) | .4868(4) | −.0019(5) | .3559(3) | .065(2) |
| C(15) | .4070(6) | .01811(10) | .3592(6) | .082(3) |
| C(16) | .4953(7) | .2564(8) | .3624(6) | .079(3) |
| O(16) | .4841(5) | .3639(6) | .4015(4) | .095(2) |
| C(16M) | .5697(8) | .4308(10) | .4288(7) | .102(3) |
| C(17) | .5056(6) | .2802(9) | .2841(6) | .073(3) |
| C(17M) | .4268(7) | .3541(11) | .2307(6) | .103(4) |
| C(18) | .5806(7) | .2368(10) | .2680(6) | .079(3) |
| C(19) | .6018(7) | .2458(11) | .1964(6) | .092(3) |
| C(20) | .6768(8) | .1937(12) | .1809(6) | .097(3) |
| C(21) | .7032(8) | .2069(13) | .1094(7) | .111(4) |
| C(22) | .7771(8) | .1565(15) | .0948(7) | .121(5) |
| C(23) | .8086(8) | .1781(16) | .0240(6) | .128(5) |
| C(23M) | .7254(9) | .2152(23) | −.0474(7) | .184(9) |
| C(24) | .8912(8) | .2643(18) | .0406(6) | .140(6) |
| C(25) | .9826(9) | .2329(20) | .1069(6) | .141(6) |
| C(25M) | 1.0348(12) | .1245(20) | .0884(8) | .178(8) |
| C(26) | 1.0512(10) | .3412(22) | .1293(7) | .157(8) |
| O(26) | 1.1132(8) | .3601(21) | .0998(7) | .281(11) |
| C(27) | 1.0375(8) | .4278(16) | .1891(7) | .118(5) |
| O(27) | 1.0877(7) | .5366(13) | .1901(7) | .185(5) |
| C(27M) | 1.0445(17) | .6202(22) | .1382(13) | .256(13) |
| C(28) | 1.0824(7) | .3750(11) | .2699(6) | .091(3) |
| O(28) | 1.1827(4) | .3501(7) | .2818(4) | .108(2) |
| C(29) | 1.0329(7) | .2733(10) | .2922(5) | .073(3) |
| C(29M) | .9318(6) | .2995(10) | .2984(6) | .094(3) |
| C(30) | 1.0764(7) | .1700(10) | .3100(5) | .077(3) |
| C(31) | 1.0376(7) | .0581(10) | .3340(5) | .081(3) |
| C(31M) | 1.0198(9) | −.0385(13) | .2723(7) | .124(4) |
| C(32) | 1.1046(7) | .0210(10) | .4103(6) | .079(3) |
| O(32) | 1.1436(7) | −.0747(9) | .4183(5) | .132(5) |
| C(33) | 1.1271(6) | .1025(9) | .4776(5) | .071(3) |
| C(34) | 1.0764(5) | .0601(8) | .5342(5) | .062(2) |
| O(34) | .9735(3) | .0853(5) | .4967(3) | .071(2) |
| C(35) | 1.1115(5) | .1217(9) | .6132(5) | .064(2) |
| C(35M) | 1.1060(7) | .2562(10) | .6069(6) | .092(3) |
| C(36) | 1.2149(6) | .0757(9) | .6578(5) | .072(3) |
| C(37) | 1.2650(6) | .1298(9) | .7370(5) | .074(3) |
| C(38) | 1.2091(7) | .1198(14) | .7935(5) | .110(4) |
| C(39) | 1.2680(9) | .1650(16) | .8735(6) | .128(5) |
| O(39) | 1.2082(8) | .1584(20) | .9206(6) | .243(9) |
| C(39M) | 1.2099(20) | .2512(47) | .9702(17) | .498(36) |
| C(40) | 1.3640(9) | .0982(13) | .9048(6) | .0116(4) |
| O(40) | 1.4177(7) | .1412(10) | .9790(5) | .151(4) |
| C(41) | 1.4221(7) | .1138(13) | .8506(6) | .110(4) |
| C(42) | 1.3653(6) | .0697(11) | .7702(5) | .096(3) |
| C(43) | 1.4272(14) | .0621(20) | 1.0408(9) | .171(7) |
| C(44) | 1.5146(20) | −.0307(24) | 1.0549(10) | .238(12) |
| O(45) | 1.4956(12) | −.1215(13) | .9899(7) | .215(5) |

(U(eq) is defined as one third of the trace of the orthogonalized Uij tensor)

TABLE 2

Bond lengths (Å)

| | | | |
|---|---|---|---|
| C(1)-O(1) | 1.193(10) | C(24)-C(25) | 1.52(2) |
| C(1)-O(34) | 1.329(10) | C(25)-C(25M) | 1.53(2) |
| C(1)-C(2) | 1.545(11) | C(25)-C(26) | 1.54(3) |
| C(2)-N(7) | 1.465(10) | C(26)-O(26) | 1.20(2) |
| C(2)-C(3) | 1.500(13) | C(26)-C(27) | 1.53(2) |
| C(3)-C(4) | 1.511(14) | C(27)-O(27) | 1.42(2) |
| C(4)-C(5) | 1.502(13) | C(27)-C(28) | 1.533(14) |
| C(5)-C(6) | 1.518(14) | O(27)-C(27M) | 1.34(2) |
| C(6)-N(7) | 1.453(10) | C(28)-O(28) | 1.415(10) |
| N(7)-C(8) | 1.315(9) | C(28)-C(29) | 1.471(14) |
| C(8)-O(8) | 1.237(9) | C(29)-C(30) | 1.311(13) |
| C(8)-C(9) | 1.523(11) | C(29)-C(29M) | 1.523(12) |
| C(9)-O(9) | 1.178(9) | C(30)-C(31) | 1.497(14) |
| C(9)-C(10) | 1.532(11) | C(31)-C(32) | 1.482(13) |
| C(10)-O(10) | 1.398(9) | C(31)-C(31M) | 1.53(2) |
| C(10)-O(14) | 1.425(10) | C(32)-O(32) | 1.201(11) |
| C(10)-C(11) | 1.540(11) | C(32)-C(33) | 1.487(13) |
| C(11)-C(11M) | 1.491(13) | C(33)-C(34) | 1.521(11) |
| C(11)-C(12) | 1.546(12) | C(34)-O(34) | 1.447(9) |
| C(12)-C(13) | 1.51(2) | C(34)-C(35) | 1.537(11) |
| C(13)-C(14) | 1.506(13) | C(35)-C(35M) | 1.517(13) |
| C(14)-O(14) | 1.441(10) | C(35)-C(36) | 1.540(11) |
| C(14)-C(15) | 1.516(14) | C(36)-C(37) | 1.525(12) |
| C(15)-C(16) | 1.511(12) | C(37)-C(38) | 1.503(11) |
| C(16)-O(16) | 1.439(11) | C(37)-C(42) | 1.532(12) |
| C(16)-C(17) | 1.512(14) | C(38)-C(39) | 1.526(14) |
| O(16)-C(16M) | 1.392(11) | C(39)-O(39) | 1.399(13) |
| C(17)-C(18) | 1.301(12) | C(39)-C(40) | 1.51(2) |
| C(17)-C(17M) | 1.491(13) | O(39)-C(39M) | 1.38(4) |
| C(18)-C(19) | 1.441(14) | C(40)-O(40) | 1.417(13) |
| C(19)-C(20) | 1.333(14) | C(40)-C(41) | 1.50(2) |
| C(20)-C(21) | 1.48(2) | O(40)-C(43) | 1.41(2) |
| C(21)-C(22) | 1.30(2) | C(41)-C(42) | 1.521(14) |
| C(22)-C(23) | 1.52(2) | C(43)-C(44) | 1.59(3) |
| C(23)-C(24) | 1.49(2) | C(44)-O(45) | 1.52(2) |
| C(23)-C(23M) | 1.52(2) | | |

TABLE 3

Bond angles (°)

| | | | |
|---|---|---|---|
| O(1)-C(1)-O(34) | 125.1(7) | C(23)-C(24)-C(25) | 116(2) |
| O(1)-C(1)-C(2) | 126.8(8) | C(24)-C(25)-C(25M) | 111.7(14) |
| O(34)-C(1)-C(2) | 108.0(8) | C(24)-C(25)-C(26) | 110(2) |
| N(7)-C(2)-C(3) | 111.5(6) | C(25M)-C(25)-C(26) | 111.9(12) |
| N(7)-C(2)-C(1) | 111.3(7) | O(26)-C(26)-C(27) | 120(2) |
| C(3)-C(2)-C(1) | 110.4(7) | O(26)-C(26)-C(25) | 122(2) |
| C(2)-C(3)-C(4) | 111.6(9) | C(27)-C(26)-C(25) | 118.5(12) |
| C(5)-C(4)-C(3) | 111.8(9) | O(27)-C(27)-C(26) | 112.2(12) |
| C(4)-C(5)-C(6) | 110.6(7) | O(27)-C(27)-C(28) | 105.4(12) |
| N(7)-C(6)-C(5) | 111.4(8) | C(26)-C(27)-C(28) | 109.5(12) |
| C(8)-N(7)-C(6) | 123.5(7) | C(27M)-O(27)-C(27) | 118.5(14) |
| C(8)-N(7)-C(2) | 118.6(7) | O(28)-C(28)-C(29) | 111.3(9) |
| C(6)-N(7)-C(2) | 117.3(6) | O(28)-C(28)-C(27) | 108.7(8) |
| O(8)-C(8)-N(7) | 123.6(7) | C(29)-C(28)-C(27) | 118.4(10) |
| O(8)-C(8)-C(9) | 115.6(7) | C(30)-C(29)-C(28) | 121.5(9) |
| N(7)-C(8)-C(9) | 120.8(8) | C(30)-C(29)-C(29M) | 122.9(10) |
| O(9)-C(9)-O(8) | 121.3(7) | C(29)-C(29)-C(29M) | 115.4(9) |
| O(9)-C(9)-C(10) | 124.8(8) | C(29)-C(30)-C(31) | 128.7(9) |
| C(8)-C(9)-C(10) | 113.6(7) | C(32)-C(31)-C(30) | 108.8(8) |
| O(10)-C(10)-O(14) | 112.1(7) | C(32)-C(31)-C(31M) | 113.7(10) |

TABLE 3-continued

Bond angles (°)

| | | | |
|---|---|---|---|
| O(10)-C(10)-C(9) | 109.7(6) | C(30)-C(31)-C(31M) | 111.8(8) |
| O(14)-C(10)-C(9) | 100.5(6) | O(32)-C(32)-C(31) | 120.3(11) |
| O(10)-C(10)-C(11) | 108.1(6) | O(32)-C(32)-C(33) | 118.8(10) |
| O(14)-C(10)-C(11) | 111.6(6) | C(31)-C(32)-C(33) | 120.8(9) |
| C(9)-C(10)-C(11) | 114.9(7) | C(32)-C(33)-C(34) | 110.2(8) |
| C(11M)-C(11)-C(10) | 114.3(7) | O(34)-C(34)-C(33) | 104.8(6) |
| C(11M)-C(11)-C(12) | 111.2(8) | O(34)-C(34)-C(35) | 109.8(6) |
| C(10)-C(11)-C(12) | 107.9(7) | C(33)-C(34)-C(35) | 114.5(7) |
| C(13)-C(12)-C(11) | 111.9(8) | C(1)-O(34)-C(34) | 119.2(7) |
| C(14)-C(13)-C(12) | 109.9(9) | C(35M)-C(35)-C(34) | 112.6(8) |
| O(14)-C(14)-C(13) | 109.8(8) | C(35M)-C(35)-C(36) | 113.2(8) |
| O(14)-C(14)-C(15) | 106.2(7) | C(34)-C(35)-C(36) | 108.6(7) |
| C(13)-C(14)-C(15) | 113.2(8) | C(37)-C(36)-C(35) | 116.9(8) |
| C(10)-O(14)-C(14) | 115.1(6) | C(38)-C(37)-C(36) | 115.6(7) |
| C(16)-C(15)-C(14) | 114.5(7) | C(38)-C(37)-C(42) | 109.6(8) |
| O(16)-C(16)-C(15) | 105.4(7) | C(36)-C(37)-C(42) | 107.5(8) |
| O(16)-C(16)-C(17) | 112.5(8) | C(37)-C(38)-C(39) | 112.5(8) |
| C(15)-C(16)-C(17) | 113.4(8) | O(39)-C(39)-C(40) | 113.9(13) |
| C(16M)-O(16)-C(16) | 114.0(7) | O(39)-C(39)-C(38) | 108.2(10) |
| C(18)-C(17)-C(17M) | 124.9(9) | C(40)-C(39)-C(38) | 111.0(11) |
| C(18)-C(17)-C(16) | 119.2(9) | C(39)-O(39)-C(39M) | 119(2) |
| C(17M)-C(17)-C(16) | 115.9(8) | O(40)-C(40)-C(41) | 110.3(10) |
| C(17)-C(18)-C(19) | 127.7(10) | O(40)-C(40)-C(39) | 110.2(12) |
| C(20)-C(19)-C(18) | 125.6(11) | C(41)-C(40)-C(39) | 108.9(10) |
| C(19)-C(20)-C(21) | 126.6(11) | C(43)-O(40)-C(40) | 115.9(12) |
| C(22)-C(21)-C(20) | 126.3(12) | C(40)-C(41)-C(42) | 111.2(9) |
| C(21)-C(22)-C(23) | 126.0(13) | C(41)-C(42)-C(37) | 112.8(9) |
| C(24)-C(23)-C(23M) | 111(2) | O(40)-C(43)-C(44) | 114(2) |
| C(24)-C(23)-C(22) | 111.4(10) | O(45)-C(44)-C(43) | 112.2(14) |
| C(23)-C(23)-C(22) | 114.2(10) | | |

What is claimed is:

1. A composition comprising a rapamycin derivative selected from the group consisting of 40-O-(2-hydroxy)ethyl-rapamycin, 40-O-(3-hydroxy)propyl-rapamycin, and 40-O-[2-(2-hydroxy)ethoxy]ethyl-rapamycin, or rapamycin; and an antioxidant selected from the group consisting of 2,6-di-tert.-butyl-4-methylphenol, vitamin C, and combinations thereof, wherein the rapamycin derivative or rapamycin is in crystalline form.

2. The composition according to claim 1 wherein the 40-O-(2-hydroxy)ethyl-rapamycin has a crystal lattice a=14.37 Å, b=11.24 Å, c=18.31 Å, the volume being 2805 Å$^3$.

3. The composition according to claim 1 wherein the antioxidant is present in an amount of up to 1 weight percent, based on the weight of the rapamycin derivative or rapamycin.

4. The composition according to claim 3 wherein the antioxidant is present in an amount of 0.2 weight percent.

5. The composition according to claim 1 wherein the antioxidant is 2,6-di-tert.-butyl-4-methylphenol.

* * * * *

UNITED STATES PATENT AND TRADEMARK OFFICE
CERTIFICATE OF CORRECTION

PATENT NO. : 6,605,613 B2
DATED : August 12, 2003
INVENTOR(S) : Navarro et al.

It is certified that error appears in the above-identified patent and that said Letters Patent is hereby corrected as shown below:

<u>Title page,</u>
Item [*] Notice, should read:

-- [*] Notice: Subject to any disclaimer, the term of this patent is extended or adjusted under 35 U.S.C. 154(b) by 47 days. --

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO.       : 6,605,613 B2                                                    Page 1 of 1
APPLICATION NO.  : 09/866977
DATED            : August 12, 2003
INVENTOR(S)      : Navarro et al.

It is certified that error appears in the above-identified patent and that said Letters Patent is hereby corrected as shown below:

Title page,

[*] Notice:    Subject to any disclaimer, the term of this patent is extended or adjusted under 35 USC 154(b) by (47) days Delete the phrase "by 47 days" and insert -- by 0 days--

Signed and Sealed this

Twenty-third Day of October, 2007

JON W. DUDAS
*Director of the United States Patent and Trademark Office*